United States Patent
McGrath et al.

(10) Patent No.: US 9,393,350 B2
(45) Date of Patent: Jul. 19, 2016

(54) ULTRAVIOLET ACTIVATED ANTIMICROBIAL SURFACES

(71) Applicant: METASCAPE, LLC, Maple Grove, MN (US)

(72) Inventors: Terrence S. McGrath, Wellton, AZ (US); Deidre Sewell, Fort Collins, CO (US); Daniel M. Storey, Longmont, CO (US)

(*) Notice: Subject to any disclaimer, the term of this patent is extended or adjusted under 35 U.S.C. 154(b) by 59 days.

(21) Appl. No.: 14/149,271

(22) Filed: Jan. 7, 2014

(65) Prior Publication Data

US 2014/0127391 A1 May 8, 2014

Related U.S. Application Data

(63) Continuation of application No. 11/542,531, filed on Oct. 3, 2006, now Pat. No. 8,623,446.

(60) Provisional application No. 60/776,537, filed on Feb. 25, 2006.

(51) Int. Cl.

| | |
|---|---|
| A61L 29/10 | (2006.01) |
| C02F 1/32 | (2006.01) |
| C23C 4/10 | (2016.01) |
| C23C 14/06 | (2006.01) |
| C23C 14/18 | (2006.01) |
| C23C 14/20 | (2006.01) |

(Continued)

(52) U.S. Cl.
CPC .................. *A61L 29/106* (2013.01); *C02F 1/32* (2013.01); *C23C 4/10* (2013.01); *C23C 14/0688* (2013.01); *C23C 14/18* (2013.01); *C23C 14/205* (2013.01); *C23C 14/325* (2013.01); *C23C 14/54* (2013.01)

(58) Field of Classification Search
CPC .............. C02F 1/32; C23C 4/10; C23C 14/32
USPC ........... 210/758; 427/453, 595, 597, 576, 446
See application file for complete search history.

(56) References Cited

U.S. PATENT DOCUMENTS

| | | | |
|---|---|---|---|
| 4,265,747 A * | 5/1981 | Copa | A61L 2/14 210/758 |
| 4,443,488 A | 4/1984 | Little et al. | |
| 4,677,143 A | 6/1987 | Laurin et al. | |

(Continued)

FOREIGN PATENT DOCUMENTS

WO    WO 03/048333    6/2003

OTHER PUBLICATIONS

Salama, G., et al., "Silver ions trigger $Ca^{2+}$ release by acting at the apparent physiological release site in sarcoplasmic reticulum", *Journal of Biological Chemistry*, Nov. 10, 1984, pp. 13363-13369, vol. 259, No. 21.

(Continued)

*Primary Examiner* — Dah-Wei D Yuan
*Assistant Examiner* — Andrew Bowman
(74) *Attorney, Agent, or Firm* — Saliwanchik, Lloyd & Eisenschenk

(57) ABSTRACT

The invention is directed to an ion plasma deposition (IPD) method adapted to coat polymer surfaces with highly adherent antimicrobial films. A controlled ion plasma deposition (IPD) process is used to coat a metal or polymer with a selected metal/metal oxide. Exposing the coated surface to ultraviolet light significantly improves the antimicrobial properties of the deposited coatings.

17 Claims, 3 Drawing Sheets

(51) Int. Cl.
*C23C 14/32* (2006.01)
*C23C 14/54* (2006.01)

(56) References Cited

U.S. PATENT DOCUMENTS

| | | | |
|---|---|---|---|
| 5,454,886 A | 10/1995 | Burrell et al. | |
| 6,235,351 B1 * | 5/2001 | DiMarzio | C23C 4/10 427/446 |
| 6,313,064 B1 | 11/2001 | Miyafuji et al. | |
| 6,846,556 B2 | 1/2005 | Boire et al. | |
| 2002/0068167 A1 | 6/2002 | Veerasamy | |
| 2002/0127404 A1 | 9/2002 | Veerasamy | |
| 2003/0143335 A1 | 7/2003 | Qiu et al. | |
| 2003/0162163 A1 | 8/2003 | Burgess et al. | |
| 2005/0003019 A1 * | 1/2005 | Petersen | A01N 59/16 424/617 |

OTHER PUBLICATIONS

Russell, A. D., et al., "Antimicrobial Activity and Action of Silver", *Progress in Medicinal Chemistry*, 1994, pp. 351-370, vol. 31, G. P. Ellis & D. K. Luscombe, ed., Elsevier Science B. V.

Kumar, R. S., et al., "Antioxidant and antimicrobial activities of *Bauhinia racemosa* L. stem bark", *Brazilian Journal of Medical and Biological Research*, Jul. 2005, pp. 1015-1024, vol. 38, No. 7.

Website: http://earthobservatory.nasa.gov/Library/ChemistrySunlight.

Website: http://physics.nist.gov/cgi-bin/AtData/main_asd.

Dorau, B., et al., "An investigation into the potential of ionic silver as a wood preservative", *Proceedings from the Woodframe Housing Durability and Disasters Issues Conference*, Oct. 4-6, 2004, pp. 133-145, Las Vegas, Nevada.

Joyce-Wohrmann, R. M., et al., "Determination of the silver ion release from polyurethanes enriched with silver", *Infection*, 1999, pp. 46-48, vol. 27, Supp. 1.

Foote, C.S.; et al., "Properties and reactions of singlet dioxygen," *Active Oxygen in Chemistry*. 1995, pp. 105-141, Black Academic and Professional, London.

* cited by examiner

ULTRAVIOLET ACTIVATED ANTIMICROBIAL SURFACES

This application is a continuation of U.S. application Ser. No. 11/542,531, filed Oct. 3, 2006, now U.S. Pat. No. 8,623,446, which claims benefit of U.S. Provisional Application Ser. No. 60/776,537, filed Feb. 25, 2006, which is incorporated herein in its entirety.

BACKGROUND OF THE INVENTION

1. Field of the Invention

The invention relates to light induced activation of metal coated surfaces and in particular to the enhancement of antimicrobial properties of selected metal/metal oxide coated surfaces.

2. Description of Background Art

Metallic silver, silver oxides, and silver salts are highly effective antimicrobials which control infection by killing bacteria and viruses at wound sites. Silver ions block infection by forming insoluble compounds within the cell walls, blocking respiratory chains, and binding and denaturing bacterial DNA, thereby preventing replication. Silver-based biocides have also shown activity against decay fungi, some common molds and some insects due to interference with microbes in the insect gut (Dorau, et al., 2004).

Ionic silver is recognized as an effective bactericide at levels of about 0.1 µg/L while fungicidal activity requires levels on the order of about 1.9 µg/L (Joyce-Wohrmann and Mustedt, 1999). Silver ions disrupt microbial cell walls and can also damage cell receptors by binding metabolically ineffective compounds to cell pathways. To maintain effectiveness against bacterial growth, silver ions must be released continuously at effective levels in order to compensate for decrease in effective concentration due to these binding interactions. On the other hand, release of excessively high concentrations of silver can harm healthy mammalian cells so that release profiles need to be taken into consideration when antimicrobial coatings are manufactured.

Silver exhibits antimicrobial activity against most pathogens and there do not appear to be any reports of allergic reactions by patients (Russell and Hugo, 1994). Silver based coatings thus would appear to be candidates for use on surfaces of implanted medical devices in view of the tendency of in vivo devices to harbor serious infections. Applications of silver/silver oxide coatings have included hydrogels imbedded with silver compounds, wet chemistry using silver salts and antimicrobial compounds, and plasma vapor deposited surfaces of silver, cast silver, and cryogenically applied silver.

Unfortunately, medical devices and implants are ideal surfaces for primary bacterial adherence and biofilm formation. Valves and catheters for example provide hard surfaces in warm, moist, nutrient-rich environments. Biofilms, once formed, are very difficult to eradicate. Over 1,500-fold concentrations of an antimicrobial agent may be required to kill bacteria established in a biofilm compared to the amount required for treatment of free floating or planktonic forms of bacteria.

A recent upsurge in antibiotic resistant bacteria has again focused attention on the antimicrobial properties of silver and silver oxide. While some studies suggest that silver-protected surfaces on medical devices and implants may well be a preferred method of fighting infection, practical and long-term effective coating methods have yet to be developed (Tobler and Warner, 2005).

Most hospital-acquired bloodstream infections are associated with the use of an intravascular device, such as central venous catheters. Catheter-associated bloodstream infections occur more often in intensive care unit (ICU) patients than in ward patients. The mortality rate attributable to bloodstream infections in surgical ICUs has been estimated to be as high as 35%. ICU-acquired bloodstream infections account for an estimated $40,000 increase in costs per survivor and an estimated $6,000 increase in hospital costs. (CDC Publication, 2001)

There are at least two important considerations in developing antibacterial coatings for use in medical implants. A recurring problem with silver-based coatings is flaking, peeling, or sloughing of silver from the surface of the coated substrate. Release of high levels of silver ions for an extended period of time can cause localized cell death, or necrosis. This particular problem, for example, caused St. Jude Medical to withdraw a sewn-in silver heart valve cuff from the market in 2001 when it appeared that a silver/silver oxide coating on a valve cuff prevented proper healing. [FDA Enforcement Report 000635, Mar. 29, 2000]

Even when silver-based coatings on medical devices are sufficiently adherent to avoid causing cell damage, the antimicrobial effects may be weak and/or sustained for only short periods of time. Medical implants, for example, tend to be a focus for infections and therefore would benefit from antimicrobial coatings that maintain activity for long periods of time without toxicity to normal cells.

Efforts have been made to produce medically acceptable antimicrobial coatings on medical devices. The most commonly used coating processes are sputtering, ion beam assisted deposition (IBAD), and dip processes. While there are other, less commonly employed techniques, none of these commercially used methods has provided a coating that is both stable and antimicrobially resistant for relatively long periods of time. The disadvantages of these processes are briefly summarized.

Sputtering and IBAD methods are similar except that IBAD additionally employs an ion beam that provides a more dense coating. In the IBAD process, ions are accelerated toward a target of antimicrobial material such as silver. When the ions hit the target, individual silver atoms are "knocked-off". The silver atoms react with oxygen in the plasma and are directed to the substrate and deposited. Problems with this technique include controlling the percent reacted to form AgO (the antimicrobially active form of silver), scalability, and, of most concern, lack of good adhesion.

Consistently good adhesion is one of the more frequently encountered difficulties when coatings are produced by sputtering. Sputtering is a low energy process compared to other methods such as ion plasma deposition. Because of this, incoming ions do not have sufficient energy to securely implant into the surface. In attempts to solve this issue, sputtering of an antimicrobial coating usually requires a seed layer on a substrate surface to achieve even moderate adhesion. Under static conditions, sputtering may produce an acceptably adherent film, but if the substrate is twisted, bent or exposed to bacteria in vivo, as encountered with soft tissue repair devices, the coating has a high probability of de-lamination and subsequent release of metal particles into the body. Silver particles are a serious problem because large amounts of silver concentrated in one area can cause necrosis.

Controlling the actual percent of AgO can also pose a significant problem with sputtering methods because in order to act as an effective antimicrobial, coatings need to consist of a large percentage of AgO versus $Ag_2O$. The generation of singlet oxygen is also thought to be important and has been known for years to provide antimicrobial activity due to it's free radical nature (Kumar, et al., 2005).

Scalability is also a consideration with sputtering processes when commercial quantities of coated devices are manufactured. Even when adhesion is not a significant consideration, cost reduction can only be realized by way of scalability. The sputtering process does not lend itself to large scale production, which requires complex fixturing, small throwing power, because parts need to be in close proximity to the target, and because of limitations on target size. Sputtering is an extremely slow process that has a typical deposition rate of angstroms per minute. This leads to long processing times per deposition cycle, in addition to necessary post processing to convert the non-reactive $Ag_2O$ to AgO. The area that can be treated at any one time is typically limited to 20-100 square inches. For these reasons, it is not only economically inhibiting to scale up the sputtering process, it is in practical terms physically impossible.

Dip processing is another method of depositing an antimicrobial, whether silver or non-silver based, onto the surface of medical devices. The process of depositing a liquid based coating onto a substrate is complicated. The major problems with this technique are identification of a soluble antimicrobial agent with long-lasting activity, and avoidance of uneven adherence of the agent to the substrate.

Uneven coatings on a substrate surface are generally unacceptable. With dip processes, wetting of the surface is random and spotty at best. This leads to areas that lack any antimicrobial coating and are a breeding ground for infection and biofilm formation.

Some attention has been devoted to modifying surfaces of antimicrobial coatings in the hope of increasing antimicrobial activity. Ion beams have been used to carve textures into surfaces on implants, hydrocephalic shunts, percutaneous connectors, and orthopedic prostheses. The patterns can be holes, columns, cones, or pyramids as small as one µm. These added patterns have been described as increasing a device's surface area 20 times and therefore increasing antimicrobial activity of deposited coatings, as suggested in U.S. Pat. No. 5,383,934.

Deficiencies in the Art

Deposition of antimicrobial materials is commonly limited to only a few methods for producing silver and silver oxide coatings. Each of these methods has serious disadvantages and none has been developed to efficiently produce the highly adherent, and evenly distributed antimicrobial films required for use on surfaces of medical devices and instruments. Current state of the art processes, such as sputtering, dip and ion beam assisted deposition (IBAD), produce coatings with limited adhesion to flexible substrates. Multiple layers of base coatings added to provide adhesion not only increase processing time and costs but also increase thickness, which may not be desirable.

The need for antimicrobial coatings in the medical device market is well known, especially for antimicrobial films that have broad activity over relatively long periods of time. Where medical devices are used, the coatings must also meet safety standards for in vivo use.

SUMMARY OF THE INVENTION

The present invention particularly addresses the problem of low activity in antimicrobial coatings, in addition to related problems of inefficient coating processes, and poor substrate adhesion of antibacterial coatings. Highly antimicrobially active coatings that resist flaking and peeling from substrate surfaces can be produced by the disclosed process which utilizes ion plasma deposition (IPD) in combination with ultraviolet (UV) light.

Coatings with surprisingly improved antimicrobial activities have been obtained by exposing the surface of controlled IPD deposited metal coatings to ultraviolet light. An entirely unexpected finding was that several highly adherent metal coatings which initially showed little or no antimicrobial activity could be activated when exposed to ultraviolet light in the 200-400 nm range; in some cases exhibiting antimicrobial activity only after exposure to ultraviolet light.

The invention is in part based on the development of an IPD-based method that produces predictable coating structures that have excellent adhesion, making these coatings particularly desirable for use on implanted medical devices. The method provides antimicrobial coatings that can be deposited in multiple layers of antimicrobial or antimicrobially-activated materials on metal and non-metal substrates for use in implants such as valves and indwelling catheters. The layers can be relatively thin, for example in the 100 nm range, so that production cost is reduced without sacrificing desired antimicrobial activity.

A modified IPD/UV method has been developed for preparing antimicrobial metal coatings that have significantly enhanced antimicrobial activity. The coatings are particularly adaptable for use on devices and materials used in medical applications. The coatings do not flake or peel, as is common with coatings produced by electrodeposition or magnetron sputtering. Antibacterial activity is maintained on coatings applied to polymers and various metals because flaking and peeling are not a problem. Moreover, the coatings exhibit significantly improved antibacterial activity compared with currently available antimicrobial coatings.

The antimicrobial coatings of the present invention can be applied to metals, and to polymers, which are preferred materials for medical devices such as catheters, stents, and plastic implants.

The invention provides coatings that are uniquely suitable for use on medical devices for use in the human body or veterinary applications. The IPD/UV method for producing the coatings is economical and provides high quality coatings.

DEFINITIONS

PVD is thin film deposition process in the gas phase in which source material is physically transferred in the vacuum to the substrate without any chemical reactions involved. This type of deposition includes thermal evaporation electron-beam deposition and sputtering deposition. The IPD process is a sub-segment of physical vapor deposition.

Macros and macroparticles refer to particles larger than a single ion. Small macro-particles refer to particles from two atoms to approximately 100 nanometers (alternatively, nano-particles). Medium macro-particles refer to particles from 100 nanometers to about 1 micron. Large macro-particles refer to particles larger than 1 micron.

Antimicrobial refers to the ability of a compound to destroy microbes, prevent their development, or inhibit their pathogenic action and as used herein is intended to apply to bacteria, yeast and other fungi.

IPD, as used in the context of experiments and methods described herein, refers to an ionic plasma deposition process that uses a modified controlled cathodic arc discharge on a target material to create highly energized plasma. IPD differs from normal cathodic arc processes described by others in that the deposition of particle size is highly controlled.

The term about as used herein is intended to indicate that a specified number is not necessarily exact but may be higher or lower within a 10% range as determined by the particular procedure or method used.

The term "a" as used in the claims is not intended to limit to a single species.

As used herein, "substantially free" does not necessarily mean entirely free; rather that the amount of material present will not significantly affect properties claimed for the absence of the material.

DETAILED DESCRIPTION

Figure 1:
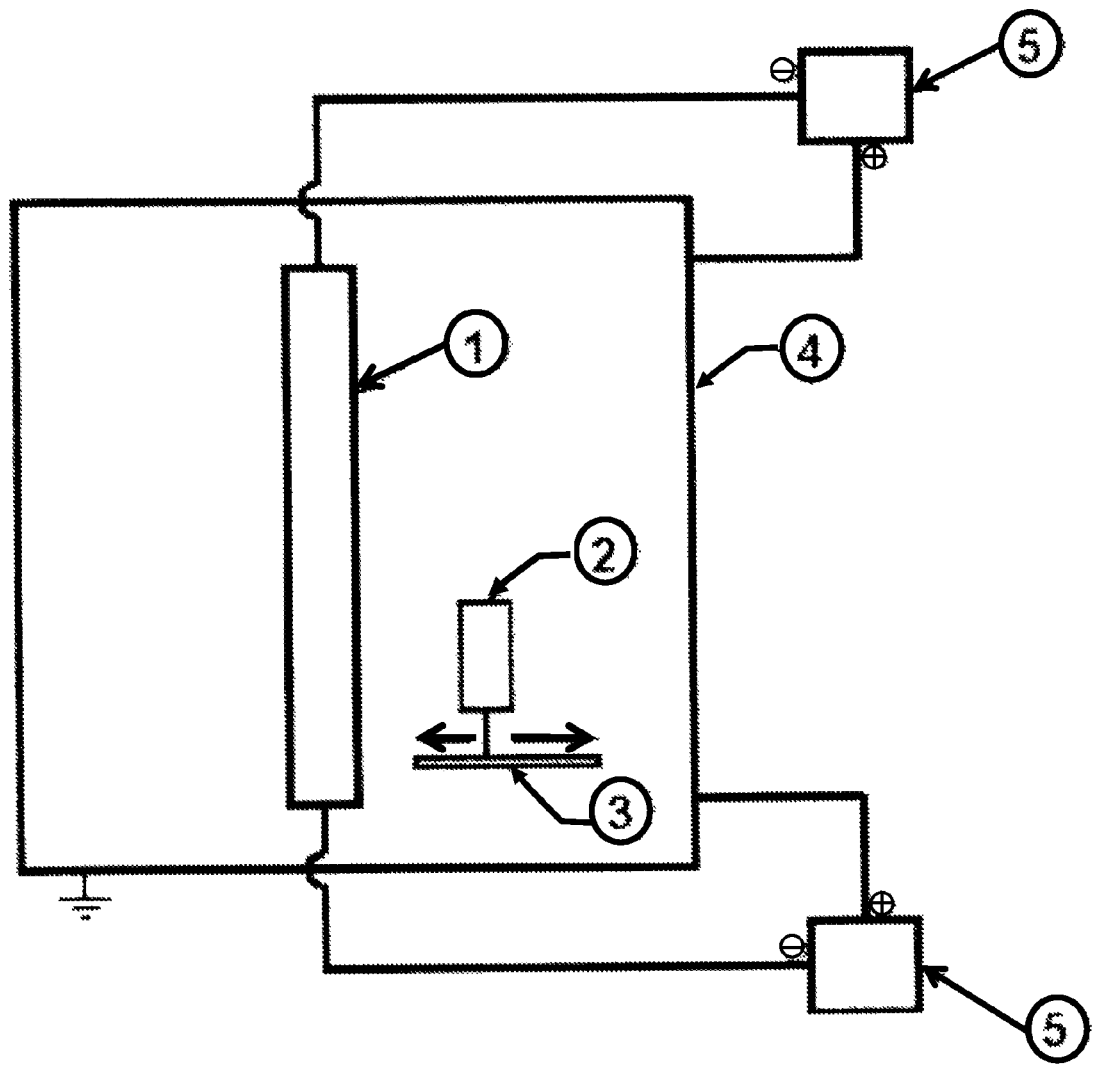
FIG. 1 is a sketch of the IPD apparatus. Target material (1), substrate being coated (2), mechanism for moving the substrate closer and further away from the target (3), vacuum chamber (4), power supply for the target (5).

The invention is directed to the use of ultraviolet radiation in combination with highly controlled IPD conditions to achieve stable highly antibacterial coated substrates. It is the combination of an IPD method for macroparticle deposition and the discovery of the use of specific wavelengths of ultraviolet (UV) light that provides the unique aspects of the present invention. The significant improvement in antimicrobial activity of surface coatings is based on the structural features of the deposited materials, the method with which the IPD is controlled, and ultraviolet light activation of the coating surface.

The antimicrobial coatings prepared by the new method may be deposited from any of a number of metals, or combinations of metals that are suitable for ion deposition. Elements include those having an atomic number greater then 21, and a density greater then 4.5 g/cm$^2$, e.g., Ti, Zr, Cr, Co, Ni, Mo, Pd, Ag, Hf, Ta, W, Ir, Pt, Sn, Bi, Zn, Au, and alloys and compounds of these metals. For commercial biological applications, use of silver, copper, gold, titanium and hafnium are preferred metals. Target materials may also include AgO, TiO, $TiO_2$, CuO, HfN and higher oxidation forms of silver, copper, and titanium, which may in some cases be more highly antimicrobial compared to lower oxides of these metals. The disclosed IPD-UV process provides highly conformed, adherent, thin, highly antimicrobial coatings, using tunable controls that provide antimicrobial activities within ranges that are typically necessary in medical applications.

Some deposited metals, such as surface film deposited titanium dioxide ($TiO_2$) do not exhibit antimicrobial activity when deposited by conventional deposition or standard plasma arc deposition. The deposition/surface activation method described herein provides an antimicrobially active surface, as demonstrated in the Examples using the IPD/UV process. An initially inactive deposited $TiO_2$ surface can be activated to an antimicrobially active surface by the UV process.

Highly adherent antimicrobial coatings have been produced using a modified ion deposition method. The process utilizes a controlled deposition system in combination with substrate exposure to ultraviolet (UV) light.

The disclosed modified IPD process itself generates a significant level of UV photons and high-energy ions when oxygen is present in the system. The spectral profile of the UV energy emitted from the source (target) is determined by the specific metal(s) or alloy(s) used. A high-energy coulomb explosion excites diatomic oxygen ($O_2$) gas injected into the chamber with a broad range of UV energy, causing the two oxygen atoms of ground state oxygen to dissociate, yielding singlet oxygen. Ground state oxygen is a triplet where at least two electron orbits are unpaired and parallel (Foote, 1995). Singlet oxygen is a singlet molecule (O*) that has undergone an electron spin inversion to pair all the electrons in the oxygen atom. Some of the differences in bonding properties arise because triplet oxygen is paramagnetic while singlet oxygen is slightly magnetic.

Molecules whose outermost pair of electrons have parallel spins, symbolized by ↑↑, are in the "triplet" state; molecules whose outermost pair of electrons have anti-parallel spins, symbolized by ↑↓, are in the "singlet" state. Ground-state oxygen is in the triplet state, indicated by the superscripted "3" in $^3O_2$; its two unpaired electrons have parallel spins, a characteristic that, according to rules of physical chemistry, does not allow them to react with most molecules. Thus, ground-state or triplet oxygen is not very reactive. However, triplet oxygen can be activated by the addition of energy, and transformed into reactive oxygen species.

Relative intensities of the spectral lines observed for any element depend upon the light source and excitation conditions. Thus, even if the relative intensities observed in a particular experiment are adjusted to correct for the wavelength dependence of the sensitivity of the spectrometer and detector, the intensities will in general be different from relative intensities from previous observation or tabulated in a compilation such as illustrated in Tables 1-3.

Ultraviolet radiation at wavelengths shorter than 242 nm splits molecular oxygen into atomic oxygen. When the energetically excited individual oxygen atoms encounter molecular oxygen, ozone ($O_3$) can form from the bonding of three-oxygen molecules. Shorter wavelengths in the UV region match several levels of singlet oxygen excitation, resulting in unique modifications to the electron orbit structure. At higher energy levels it is also possible to excite electrons from the oxygen orbital into higher levels, giving rise to efficient absorption in the range of 180-200 nm, the "Schumann-Runge bands." (http://earthobservatory.nasa.gov/Library/ChemistrySunlight/).

Each target used in the IPD process has its own spectral absorption and emission profile and is capable of generating energy within the UV range to provide the required energy for singlet oxygen formation. Listed below are representative vacuum emission spectral lines associated with a representative group of refractory metals. As shown, silver, and copper arcs yield UV in the Schumann-Runge bands, while titanium has a higher UV range which is still sufficient to yield singlet oxygen. The frequencies shown have been selected from the first excitation level of the atom and are shown as relative intensities. Less prominent wavelengths are not listed and relative intensities are shown only to indicate the stronger emissions in the near UV range of 160 nm to 140 nm (http://physics.nist.gov/cgi-bin/AtData/main_asd).

TABLE 1

Emission spectra from a silver arc in vacuum.
SILVER 1

| Wavelength Vac. (nm) | Relative Intensity |
|---|---|
| 165.152 | 60 |
| 165.210 | 50 |
| 170.927 | 50 |
| 184.771 | 20 |
| 206.183 | 200 |
| 207.051 | 100 |
| 231.027 | 30 |
| 237.574 | 50 |

TABLE 2

Emission spectra from a copper arc in vacuum
COPPER 1

| Wavelength Vac. (nm) | Relative Intensity |
|---|---|
| 165.532 | 30 |
| 168.809 | 30 |
| 169.108 | 30 |
| 170.384 | 30 |
| 171.336 | 50 |
| 172.566 | 50 |
| 174.157 | 50 |
| 177.482 | 200 |
| 182.535 | 100 |
| 216.577 | 1300 |
| 217.962 | 1600 |
| 218.240 | 1700 |
| 220.027 | 1700 |
| 220.044 | 1300 |
| 222.639 | 2100 |
| 229.455 | 2500 |
| 230.383 | 1000 |
| 239.336 | 2500 |

TABLE 3

Emission spectra from a titanium arc in vacuum.
TITANIUM 1

| Wavelength Vac. (nm) | Relative Intensity |
|---|---|
| 227.7401 | 130 |
| 228.0669 | 190 |
| 230.0567 | 150 |
| 230.3457 | 140 |
| 230.6397 | 190 |
| 238.5246 | 35 |

Activation of singlet oxygen is inherent in the IPD process due to the high energies involved. For some materials such as silver oxide, this is sufficient to impart limited antimicrobial activity by increasing the amount of antimicrobially active oxide (AgO). For other deposited surfaces, such as CuO, TiO or $TiO_2$, another mode of activating the singlet form can be used to obtain antimicrobial activity. It has been discovered that using selected wavelengths of UV light will excite these metals and metal oxides, which elevates oxygen to the singlet state, thereby creating a coated surface with new or enhanced antimicrobial properties.

The IPD/UV process can include up to at least 20% more diatomic oxygen or nitrogen into the coating surface compared to traditional IPD deposition. Oxygen or nitrogen inclusion is enhanced by first creating an oxygen or nitrogen rich plasma before introducing ultraviolet light into the plasma. This causes diatomic oxygen or nitrogen to incorporate into the substrate surface in a stable form. This results in enhanced antimicrobial activity due to the presence of singlet oxygen or nitrogen which is produced by the dissociation of diatomic oxygen or nitrogen.

It was recognized that an IPD process could be modified to provide a number of advantages over other methods commonly used for coating processes. Several basic features of a plasma arc process have been modified and exploited in developing the IPD/UV process. Unique coatings can now be prepared which have increased surface area due to controlled particle size and significantly increased antimicrobial activity. Several metal/metal oxide coated substrates in addition to silver/silver oxide have been prepared and demonstrated to have new or enhanced antimicrobial properties.

Plasma deposition processes release molecules from the target which deposit on a target surface as various sized clusters and individual atoms. The predominant trend in coating processing has been to adjust conditions to reduce the density and number of macro particle deposition in order to produce cleaner and more uniform films. Conventional wisdom in the industry has been that macro-particles in general are deleterious to the quality of deposited films. In contrast, the present invention clearly illustrates the advantages of increasing macro particle deposition, not only on metals but also on plastic substrates, in order to obtain adherent films that can be surface irradiated to enhance antimicrobial activity. It has also been found that, in general, higher macro particle deposition rates result in lower temperature depositions, while lower deposition rates result in higher temperature depositions. Higher deposition rates are thus advantageous in coating thermo sensitive materials such as certain plastics.

Arc control in the IPD process can be used for faster movement, which will create fewer and less dense arrays macro particles without the use of sensors or filters, or slower movement, which creates a greater number of more densely packed macro particles. This type of control also provides the option of mixing the two modes to create moderate amounts of macro particles, or creating a near macro-free coating followed by a macro-dense coating. The amount of macro-particles can be directly related to the amount of available silver that combines to form AgO, and therefore aids in the ability to tune the duration of the efficacy of the coating.

Adhesion of metals onto plastics using vapor deposition processes other than IPD, electroplating, or electro-less plating often results in loss of some physical properties of the original substrate. For most metals deposited by these processes, adhesion is dependent on a strike layer of titanium or chromium and even then, tends to delaminate if the substrate is bent, twisted or stretched. The IPD coating process, under the conditions described, imbeds into the substrate so adhesion is not affected by subsequent mechanical stress on the substrate.

Using controlled deposition rates, IPD can be performed at lower temperatures than most vapor deposition processes, which require a pre-heat cycle and glow discharge, the pair usually resulting in temperatures exceeding 200° C. Most plastics melt well below this temperature. The IPD process can be performed at a much lower temperature, allowing for low melting point plastics to be effectively coated without adversely affecting the original substrate specifications. Such low temperature deposition is achieved by controlling the rate at which the metal reacts with oxygen. Making more oxygen available for reaction in the system by inputting molecular oxygen or ozone allows the devices to stay cooler due to conductive cooling and slowing of the ions due to collisions.

IPD increases throughput up to 30 times compared to other plasma vapor deposition processes and dip processes, while at the same time achieving high densities and favorable antimicrobial activity. The disclosed modified IPD process for depositing an antimicrobial coating has a throughput up to ten times greater than traditional cathodic arc.

Unlike traditional PVD and dip processes, the IPD antimicrobial coatings can be scaled as large as necessary and still achieve high throughput while maintaining quality and economy of coating necessary for commercial operations.

The IPD process provides antimicrobial coatings that otherwise are not easily produced, or even possible in some cases, by traditional PVD. Some examples, not intended to be limiting, include silver oxide, copper oxide and hafnium nitride. Silver/silver oxide coatings have a higher antimicrobial activity when produced by the IPD method than the comparably active but thicker coatings obtained from more expensive processes; for example the magnetron sputtered antimicrobial coatings described by Burrell, et al. (1995). Thinner coatings, and therefore shorter processing times, can be applied using the presently disclosed IPD method to achieve at least the same antimicrobial activity as in the thicker films.

Typical PVD and electroplating are line of sight deposition methods. Because of this, it is difficult to coat complex and oddly-shaped devices without complicated fixtures, and even with the correct fixture, it may not be possible to evenly coat the devices. The modified IPD process provides non-line of sight coating but still maintains the antimicrobial qualities of the coating without the use of complicated fixtures because the coatings are readily conformed to the part.

IPD coating rates are extremely fast. With the relatively short time in the plasma to achieve a desirable antimicrobial coating, the temperature of the substrate does not rise very fast or very high. This gives an advantage over other coating methods that require cooling steps or long deposition cycles to achieve the same antimicrobial properties. The fast coating rates are also commercially attractive because higher product throughput, up to 10-fold, than with sputtering, electroplating, or IBAD processing is possible.

The new IPD/UV methods and coatings introduce several improvements to existing technology, including use of more/less macro particles to control the duration of antimicrobial coating activity, use of more reactive oxygen to increase the ratio of active to inactive silver oxide ($AgO/Ag_2O$), use of selected wavelengths of UV light during deposition to activate singlet oxygen, and the ability to lay down a thinner coating than current art allows while maintaining equivalent antimicrobial properties.

EXAMPLES

The following examples are intended to illustrate the invention and/or to provide background and are not intended to be limiting.

Methods

Antibacterial activity of the deposited coatings was tested using a zone of inhibition test (ZOI). Mueller Hinton agar was dispensed into Petri dishes. The agar plates were allowed to surface dry prior to being inoculated with a lawn of *Staphylococcus aureus* ATCC #25923. The inoculant was prepared from Bactrol Discs (Difco M.) which were reconstituted per the manufacturer's directions. Immediately after inoculation, the coated materials to be tested were placed on the surface of the agar. The dishes were incubated for 24 hr at 37° C. After the incubation period, the ZOI was measured and a corrected ZOI was calculated as follows: corrected ZOI=ZOI minus the diameter of the test material in contact with the agar.

Examples 1-3 are provided as background comparisons for the antimicrobial coatings prepared as previously reported by others. The deposition methods of the present invention (see Examples 4, et seq.) are based on a modified IPD process while the previously published comparison procedures in examples 1-3 utilize sputtering deposition.

Example 1

Antibacterial Activity of Sputtered Silver Coating on Latex

This example was performed in accordance with the coating and testing procedures described in U.S. Pat. No. 5,454,886 (the '886 patent). The method and testing were performed in accordance with the procedure detailed in Example 6 of the '886 patent.

Silver metal was deposited on 2.5 cm sections of a latex Foley catheter using a magnetron sputtering facility. Operating conditions were as follows; the deposition rate was 200 A° per minute; the argon working gas pressure was 30 m Torr; and the ratio of temperature of substrate to melting point of the coating metal silver, T/Tm was 0.30. In this example the angles of incidence were variable since the substrate was round and rough. That is, the angles of incidence varied around the circumference and, on a finer scale, across the sides and tops of the numerous surface features. The antimicrobial effect was tested by a zone of inhibition test, identical to the test described in Example 1 of the '866 patent with *S. aureus* ATCC accession number 25923 as the test organism.

The zone of inhibition (ZOI) was less than 1 mm around the catheter tubing in contrast to the 16 mm ZOI reported in the '886 patent.

Example 2

Antibacterial Activity of Sputtered Silver Coating over Teflon® on Latex

This example follows the procedures reported for preparing a Teflon®-coated latex catheter coated by DC magnetron sputtering in accordance with Example 7 in U.S. Pat. No. 5,454,886. Antimicrobial testing was performed with *S. Aureus* as described.

A Teflon coated latex Foley catheter was coated by DC magnetron sputtering 99.99% pure silver on the surface under the following conditions: 0.5 kW power, 40 mTorr $Ar/O_2$, 20° C. initial substrate temperature, a cathode/anode distance of 100 mm, and a final film thickness of 300 nm. The working gases were commercial Ar and 99/1 wt % $Ar/O_2$.

The anti-microbial effect of the coating was tested by a ZOI as described in Example 7 of the '886 patent. Mueller Hinton agar was dispensed into Petri dishes. The agar plates were allowed to surface dry prior to being inoculated with a lawn of *Staphylococcus aureus* ATCC #25923. The inoculant was prepared from Bactrol Discs (Difco, M.) which were reconstituted as per the manufacturer's directions. Immediately after inoculation, the coated materials to be tested were placed on the surface of the agar. The dishes were incubated for 24 hr. at 37° C. After the incubation period, the zone of inhibition was measured and a corrected zone of inhibition was calculated (corrected zone of inhibition=zone of inhibition-diameter of the test material in contact with the agar).

Uncoated samples showed no zone of inhibition. The coated sample showed a ZOI of less than 1 mm in contrast to the corrected ZOI of 11 mm reported in Example 7 of the '866 patent for the catheters sputtered in the 99/1 wt % Ar/$O_2$ using a working gas pressure of 40 mTorr.

Example 3

Sputtered Antibacterial Silver Coating

This example was performed in accordance with the procedure described in Example 11 in the '866 patent. Conditions used for this example included: RF magnetron power of 0.5 kW, 40 mTorr pressure, 100 mm anode/cathode distance, and 20° C.

When a working gas of argon and 20 wt % oxygen was used to sputter anti-microbial coatings under the conditions listed above, the zones of inhibition ranged from 0 to 2 mm, in contrast to the ZOI of 6 to 12 mm reported in the '866 patent Example 11.

Example 4

Control of Macro Particle Density in IPD Coatings

Control of the distance/current relationship in IPD procedures determines amount and size of the deposited macro particles. The closer the substrate is to a source (target), the more macro-particles will be present on the substrate. Macro particles evaporate as they are ejected from the target. Therefore, the longer the time of flight, the more material is evaporated from the particle. Macro particle density can also be controlled by the current because either a higher current or limiting the current to a level that occurs just before an arc split tends to cause more and larger macro particles.

A motorized unit capable of moving a substrate closer to and farther away from the target (cathode) was used to initially deposit a substantially macro-free film. This provides a base coat with excellent adhesion properties. A more macro particle dense film is then deposited by positioning the substrate closer to the target. The macro dense surface has enhanced antimicrobial activity by comparison to films having a relatively macro particle free surface. FIG. 1 illustrates an IPD apparatus indicating how the position of the substrate with respect to the target can be moved. The IPD is conducted in an oxygen atmosphere.

Figure 2:
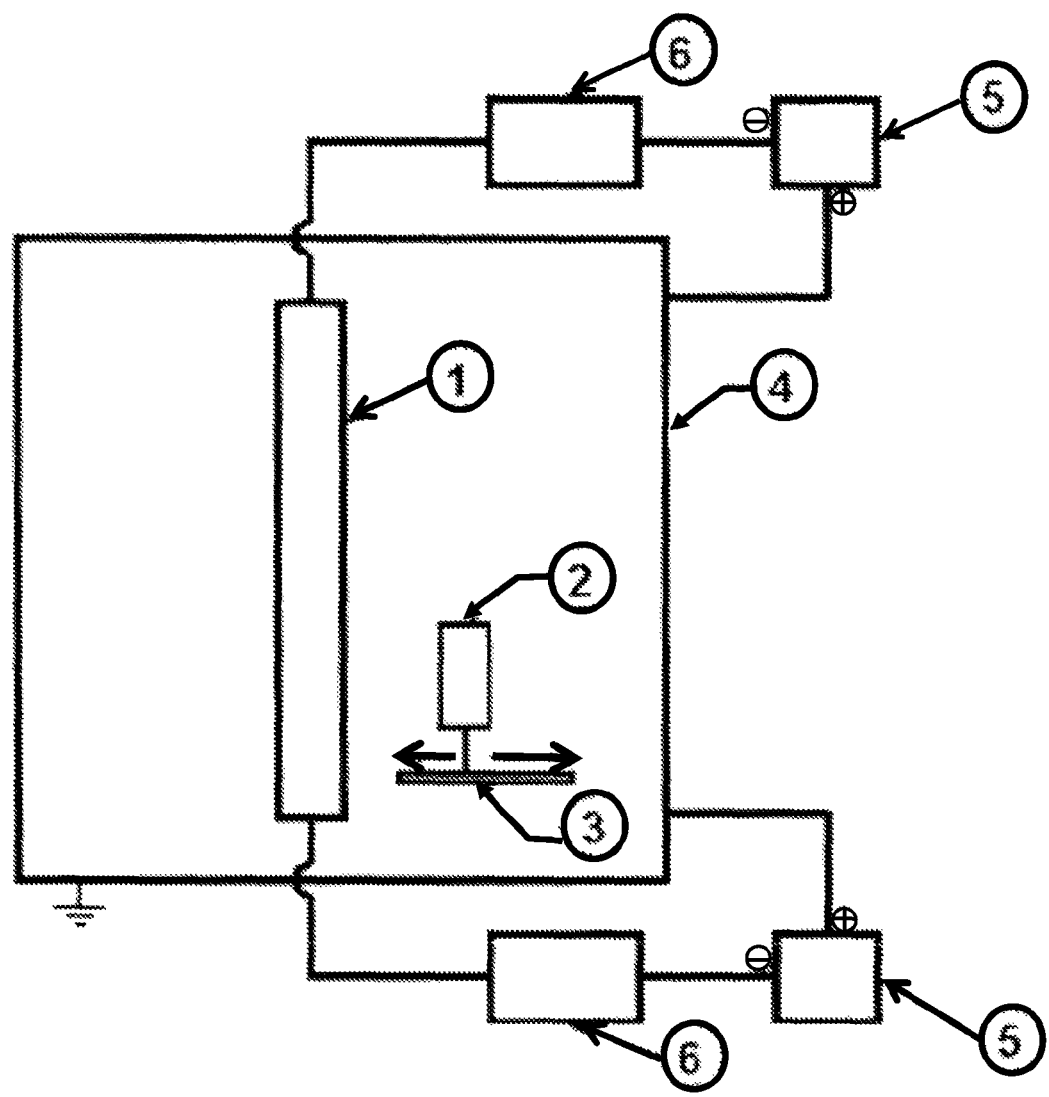
FIG. 2 is another embodiment of the IPD apparatus. Target material (1), substrate being coated (2), mechanism for moving the substrate closer and further away from the target (3), vacuum chamber (4), power supply for the target (5), device to control arc speed (6).

Macroparticle size can also be controlled by use of a variable IPD power source, which can be configured to sufficiently slow (or accelerate) the speed of the arc. The traveling speed of the arc is directly related to the amount of macro particles produced. Essentially, slowing the speed of the arc on the surface of the target (cathode) will cause it to produce more macro particles, which can be used to increase the macro particle density. Conversely, increasing the speed of the arc on the cathode will decrease production of macro particles, thereby providing more high energy ions that can be embedded into the surface of the substrate to produce better adhesion. FIG. 2 shows an IPD apparatus setup with control of arc speed and substrate position with respect to the target.

Increase and decrease travel speed of the arc can be controlled by an appropriate device such as the mechanical switch described in U.S. Pat. No. 6,936,145. The switch toggles current to two or more points on the target and is an example of one method of speed control, although other methods of control can be used. The increase and decrease of arc speed allows the deposition (without internal movement) of a substantially macro-free film for adhesion followed directly by a macro dense film by manipulation of the arc speed.

Example 5

Increasing AgO in Antimicrobial Films

An advantage of the combined IPD/UV method is that the IPD process itself can be adjusted so that more oxygen and metallic ions can be made available for combination in forming an antimicrobial film. When activated by ultraviolet light, the IPD films have significantly enhanced antimicrobial activity. The control of the plasma arc speed (see FIG. 2) can provide substantially 100% ionized oxygen plasma when the IPD is conducted in an oxygen atmosphere. The percent of singlet oxygen in the plasma can be further enhanced by injecting ozone instead of diatomic oxygen into the system. The presence of oxygen, in addition to the ability of IPD to create a highly ionized metal stream from the target means that more AgO is created films than by other methods and, in combination with exposing the deposited surface to UV light, results in significant enhancement of antimicrobial properties of metal/metal oxide coated surfaces.

Example 6

Ultraviolet Activation of IPD Deposited Ag, Ti and Cu Coatings

Figure 3:
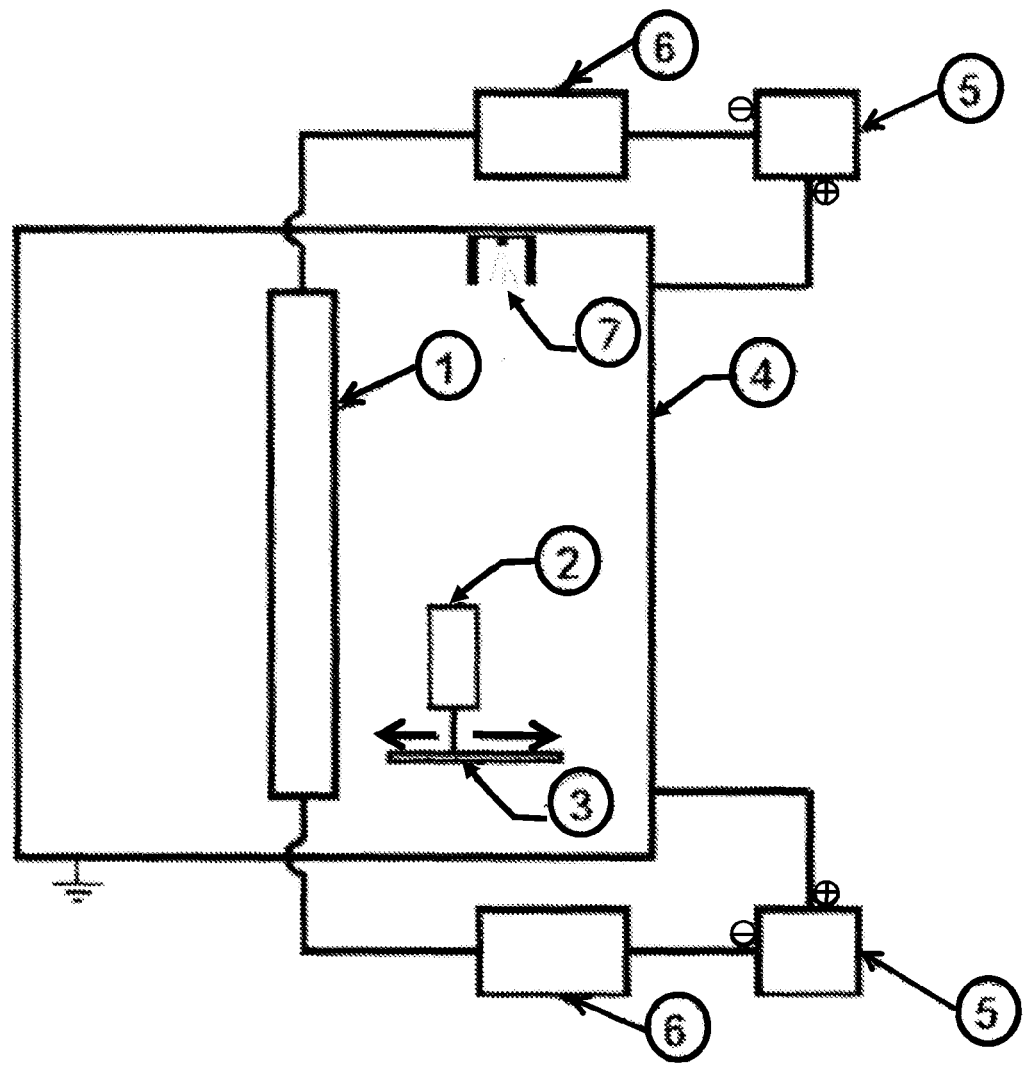
FIG. 3 is an example of the setup for a modified IPD/UV apparatus for depositing an adherent highly antimicrobial coating on a substrate. The apparatus incorporates the features of FIG. 1 and/or FIG. 2 with a source (7) to input ultraviolet light at selected wavelengths.

The additional use of UV light during or after the deposition activates singlet oxygen in silver/silver oxide deposited coatings. Silver oxide tends to relax to $Ag_2O$, the more stable form of silver oxide. UV light can also be used to activate Ti/$TiO_2$ and Cu/CuO coatings. For silver-based surfaces, UV light directed into the system converts deposited $Ag_2O$ to AgO. UV light can be supplied from a source within the vacuum chamber (FIG. 3) or from an outside source after the coated substrate is removed from the chamber.

Glass substrates were coated with 100 nm of a combination of Ag, AgO, and $Ag_2O$ using the IPD process as described in Example 4. Samples were tested by a zone of inhibition (ZOI) test on tryptic soy agar with S. aureus. Half the coated samples were incubated at 37° C. with no light exposure; the other half were incubated at 37° C. after exposure to UV light in the range of 200 to 400 nm. After a 24 hr incubation, the samples not exposed to UV showed a ZOI of up to 6 mm. The samples exposed to UV light showed a zone of inhibition of up to 12 mm, see Table 4.

Glass substrates were coated with 100 nm of a combination of Ti, TiO and $TiO_2$ using the IPD process described in Example 4. Antibacterial properties of the coated samples were tested using zone of inhibition testing on tryptic soy agar with S. aureus. Half the samples were incubated at 37° C. with no light exposure, the other half were incubated at 37° C. after exposure to Black Light Blue (BLB) in the wavelength range of 300-400 nm. After a 24 hr incubation, the samples not exposed to BLB showed no zone of inhibition. The samples exposed to BLB showed a zone of inhibition of up to 12 mm, see Table 4.

Glass substrates were coated with 100 nm of a combination of Cu, CuO, and $Cu_2O$ using the IPD process. The samples were tested by ZOI on tryptic soy agar with S. aureus. Half the samples were incubated at 37° C. with no light exposure, the other half were incubated at 37° C. after exposure to UV light in the range of 200 to 400 nm. After a 24 hr incubation, the samples not exposed to UV showed no ZOI. The samples exposed to UV all showed a ZOI. The ZOI was enhanced two-fold for the Ag-based coatings. The UV treatment on the Ti and Cu-based coatings produced antibacterial activity comparable to the Ag-based coatings where, unlike the silver coatings, no activity was observed before UV treatment. See Table 4.

TABLE 4

| Metal Combination | Coating Thickness | Light Wavelength | Microbe | ZOI (24 hr) |
|---|---|---|---|---|
| Ti, TiO, TiO2 | 100 nm | None | S. aureus | None |
| | 100 nm | None | C. albicans | None |
| | 100 nm | 300-400 nm | S. aureus | 12 mm |
| | 100 nm | 300-400 nm | C. albicans | 12 mm |
| Cu, CuO, Cu$_2$O | 100 nm | None | S. aureus | None |
| | 100 nm | None | C. albicans | None |
| | 100 nm | 200-400 nm | S. aureus | 12 mm |
| | 100 nm | 200-400 nm | C. albicans | 12 mm |
| Ag, AgO, Ag$_2$O | 100 nm | None | S. aureus | 6 mm |
| | 100 nm | None | C. albicans | 6 mm |
| | 100 nm | 200-400 nm | S. aureus | 12 mm |
| | 100 nm | 200-400 nm | C. albicans | 12 mm |

The ZOI was calculated as indicated above. This corrected ZOI is not comparable to the calculated ZOI data reported in Burrell, et al. (1995) which were measured by subtracting the dimensions of the substrate from the dimensions of the observed zone of inhibition.

REFERENCES

B. Dorau, R. Arango, F. Green III, "An investigation into the Potential of Ionic Silver as a Wood Preservative"
G. Salama, J. Abramson, "Silver ions trigger Ca$^{2+}$ release by acting at the apparent physiological release site in sarcoplasmic reticulum", J Biol Chem. 1984 Nov. 10; 259(21): 13363-9]
A. D. Russell, W. B. Hugo, "Antimicrobial Activity and Action of Silver," Progress in Medicinal Chemistry. Vol. 3, G. P. Ellis & D. K. Luscombe, ed., Elsevier Science B. V., (1994)
D. Tobler, L Warner, "Nanotech Silver Fights Microbes in Medical Devices", Medical Device & Diagnostic Industry Magazine, May 2005
Burrell, et al., U.S. Pat. No. 5,454,886 (1995)
Foote, C. S.; (1995) Properties and reactions of singlet oxygen; Active Oxygen in Chemistry. Black Academic and Professional. London. Pp. 105-141
KUMAR, R. S., SIVAKUMAR, T., SUNDERAM, R. S. et al. Antioxidant and antimicrobial activities of Bauhinia racemosa L. stem bark. Braz J Med Biol Res, July 2005, vol. 38, no. 7, p. 1015-1024.
NASA website data found at http://earthobservatory.nasa.gov/Library/ChemistrySunlight/]
NIST website; http://physics.nist.gov/cgi-bin/AtData/main-_asd
CDC Publication, Cost-Effective Infection Control Success Story: A Case Presentation, March-April 2001
Black, J. G. (1996). Microbiology, Principles and Applications, Third Edition, Prentice Hall, pp. 436-443
Dorau, B., Arango, R. and Green, F. III, "An investigation into the potential of ionic silver as a wood preservative" in Proceedings from the Woodframe Housing Durability and Disasters Issues Conference, Oct. 4-6, 2004, Las Vegas, Nev.
Joyce-Wohrmann, R. M. and Mustedt, H. Determination of the silver ion release from polyurethanes enriched with silver. Infection 27, Supp. 1, 46-48 (1999).

What is claimed is:

1. A method for producing an adherent, antimicrobial coating, comprising: depositing a first layer of ion plasma produced metal and metal oxide nanoparticulates on a substrate in a vacuum chamber, said first layer consisting of metal and metal oxide nanoparticulates substantially free of macroparticulates; depositing a second layer of ion plasma from an ion plasma source to produce metal and metal oxide macroparticulates over the first layer, said second layer consisting of mixed sizes of metal and metal oxide medium size macroparticulates ranging from 100 nm up to about 1 micron; irradiating the nanoparticulates and macroparticulates during ion plasma deposition with ultraviolet light (UV) from a separate source located in the vacuum chamber to activate ground state oxygen in the metal oxide plasma to a reactive oxygen species thereby providing an antimicrobially active coating on the substrate that is enhanced compared with the coating deposited without UV irradiation from the separate source during ion plasma deposition.

2. The method of claim 1 wherein the deposited metal and metal oxide first or second layer is selected from the group consisting of silver, gold, platinum, copper, tantalum, titanium, zirconium, hafnium, and zinc.

3. The method of claim 1 wherein the deposited metal and metal oxide first or second layer deposition is controlled by adjusting distance of the substrate holder from a cathodic arc target from which the ion plasma is generated.

4. The method of claim 3 wherein the metal and metal oxide first or second layer deposition is controlled by varying speed of the arc on the target surface.

5. The method of claim 1 wherein the metal and metal oxide first or second layer is selected from silver, copper and titanium.

6. The method of claim 1 wherein the ultraviolet light frequencies for irradiating are in the range of 200-400 nm.

7. The method of claim 1 wherein the substrate is a polymer selected from the group consisting of polypropylene, polyurethane, PTFE, polyimide, polyester, PEEK, UHMWPE, and nylon.

8. The method of claim 1 wherein the substrate is a metal selected from the group consisting of tantalum, titanium, zirconium, hafnium, silicon, iron, cobalt, chromium, zinc, alloys, and combinations thereof.

9. The method of claim 1 wherein the substrate is glass.

10. The method of claim 1 further comprising introducing ozone into the ionic plasma deposition chamber during deposition of the metal and metal oxide first and second layers.

11. The method of claim 1 wherein the first layer thickness is between about 100 nm and 1 micron.

12. The method of claim 1 wherein the metal and metal oxide first or second layer comprises Ti, TiO and TiO$_2$.

13. The method of claim 1 wherein metal and metal oxide first or second layer comprises Cu, CuO and Cu$_2$O.

14. The method of claim 1 wherein the metal and metal oxide first or second layer comprises Ag, AgO and Ag$_2$O.

15. The method of claim 1 wherein the metal and metal oxide first and second layers are independently selected from Ti/TiO/TiO$_2$, Cu/CuO/Cu$_2$O, and Ag/AgO/Ag$_2$O.

16. The method of claim 1 wherein the substrate is a medical device.

17. The method of claim 16 wherein the medical device is a stent, catheter, valve or implant.

* * * * *